(12) United States Patent
Anders et al.

(10) Patent No.: US 7,553,311 B2
(45) Date of Patent: Jun. 30, 2009

(54) MEDICAL INSTRUMENT FOR ELECTROSURGERY

(75) Inventors: Fridolin Anders, Immendingen (DE); Hubert Brueckler, Tuttlingen (DE)

(73) Assignee: Karl Storz GmbH & Co. KG (DE)

( * ) Notice: Subject to any disclaimer, the term of this patent is extended or adjusted under 35 U.S.C. 154(b) by 499 days.

(21) Appl. No.: 11/048,483

(22) Filed: Feb. 1, 2005

(65) Prior Publication Data
US 2006/0004355 A1   Jan. 5, 2006

(30) Foreign Application Priority Data
Jul. 2, 2004 (DE) .................. 20 2004 010 780 U

(51) Int. Cl.
*A61B 18/18* (2006.01)
(52) U.S. Cl. .............................. 606/51; 606/46; 606/52
(58) Field of Classification Search .................. 606/45, 606/46, 48–52
See application file for complete search history.

(56) References Cited

U.S. PATENT DOCUMENTS

| 4,502,746 | A | | 3/1985 | Wawra et al. ................ 339/3 S |
| 5,697,949 | A | * | 12/1997 | Giurtino et al. ............. 606/205 |
| 6,096,037 | A | * | 8/2000 | Mulier et al. ................. 606/49 |
| 6,152,924 | A | * | 11/2000 | Parins ........................... 606/52 |
| 6,334,860 | B1 | | 1/2002 | Dorn ............................. 606/48 |
| 6,394,998 | B1 | * | 5/2002 | Wallace et al. ................. 606/1 |
| 2002/0128649 | A1 | | 9/2002 | Bacher et al. ................. 606/46 |
| 2004/0116924 | A1 | * | 6/2004 | Dycus et al. .................. 606/51 |

FOREIGN PATENT DOCUMENTS

| DE | 3111922 C1 | 3/1981 |
| DE | 94 14996 U1 | 3/1996 |
| DE | 101 19 974 A1 | 10/2002 |
| WO | WO 98/56300 | 12/1998 |
| WO | WO 00/36986 | 6/2000 |
| WO | WO 01/15614 A1 | 3/2001 |

OTHER PUBLICATIONS

European Search Report, Apr. 12, 2005, 3 pages.

* cited by examiner

*Primary Examiner*—Michael Peffley
(74) *Attorney, Agent, or Firm*—St. Onge Steward Johnston & Reens LLC

(57) ABSTRACT

A medical instrument for electrosurgery comprises a tubular shaft having a distal end and a proximal end, at least one jaw part arranged at the distal end of the shaft and movable relative to the tubular shaft about a pivot axis, at least one electrode arranged at the at least one jaw part, and at least one current supply line leading to the at least one electrode and designed as a wire-shaped element, a distal end of which being connected to the at least one electrode, the wire-shaped element being configured as a loop in the region of the pivot axis.

11 Claims, 2 Drawing Sheets

US 7,553,311 B2

MEDICAL INSTRUMENT FOR ELECTROSURGERY

CROSS REFERENCE TO RELATED APPLICATION

The present application claims priority of German utility application no. 20 2004 0101 780.5 filed on Jul. 2, 2004.

BACKGROUND OF THE INVENTION

The invention relates to a medical instrument for electrosurgery.

Such an instrument is used, for example, for performing endoscopically assisted interventions in the human or animal body in the context of minimally invasive surgery.

With an electrosurgical medical instrument of the present invention, biological tissue can be sectioned and/or coagulated under the effect of high-frequency current. Two jaw parts, of which at least one is movable, are usually arranged at the distal end of the tubular shaft, the present invention being especially advantageous in those medical instruments in which both jaw parts are movable. Depending on the intended surgical purpose of such an instrument, the jaw parts are designed as cutting tools with cutting edges, in order to sever tissue in the body, or they are designed as gripping tools with surfaces striking bluntly against one another in order to grip severed tissue with the jaw parts and remove it from the body, or in order to hold an organ or a vessel with the aim of keeping it away from the operating site. The jaw parts can also have a combination of a cutting function and a gripping function.

If the instrument has two jaw parts, at least one of the two jaw parts is connected to the tubular shaft in an articulated manner, while the other jaw part is connected to the tubular shaft either rigidly or, once again, in an articulated manner.

In a medical instrument of the type mentioned at the outset, it is further provided that at least one jaw part has an electrode that can be acted upon with high-frequency current. If the instrument is designed as a bipolar electrosurgical instrument, as is also preferred in the context of the present invention, both jaw parts each have an electrode that can be acted upon with high-frequency current, said electrodes having different polarities. Both electrodes of the two jaw parts can accordingly be connected, separate from one another, to a respective pole of a high-frequency voltage source. By acting on the electrodes of the two jaw parts, the cutting action, in the case of a design as a cutting tool, can be increased by the thermal action of the high-frequency current in the tissue, and, on the other hand, in the case of a design as a gripping tool, tissue gripped between the jaw parts can be coagulated by the heat build-up, and bleeding of the tissue can thus be stopped.

In electrosurgical medical instruments of this type, the current supply to the at least one electrode of the at least one movable jaw part generally causes problems. In bipolar instruments in particular, the two jaw parts have to be adequately electrically insulated from one another in the area of the hinge forming the pivot axis of the at least one jaw part. An electrical separation of the two jaw parts in the area of the hinge is necessary, especially in bipolar instruments, because the electrodes of the two jaw parts are connected to different potentials. The problem of the electrical separation of the two jaw parts from one another is greater, the smaller the design of such an instrument in the area of the jaw parts and thus in the area of the hinge. However, a narrow design of the instrument in the area of the jaw parts is particularly important for minimally invasive surgery.

In an instrument known from document WO-A-00/36986, the distal end has two jaw parts, of which only one is movable, both jaw parts each having a metallic main body, which main bodies are connected to one another in an articulated manner in the area of the pivot axis. On their sides facing each other, the metallic main bodies each have an insulator element, the respective electrode of the respective jaw part being applied to these insulator elements so that the electrodes are electrically separated from the metallic main body. A current supply line runs to each of the two electrodes via the hinge, said current supply lines being designed as wire-shaped elements and being insulated from one another. In this configuration of the jaw parts, it is possible for the jaw parts in the area of the hinge to be made of metal and thus be particularly stable.

A disadvantage of this configuration is the nature of the current supply to the respective electrode in the form of the rectilinearly extending, wire-shaped element. Upon opening and closing of the jaw parts, that is to say when the at least one movable jaw part is moved, the wire-shaped element is permanently bent and stretched again. These constant changes of load occurring over the lifetime of the instrument lead relatively quickly to a fatigue fracture of the wire-shaped element in the area of the pivot axis, as a result of which the instrument does not provide a long service period, that is to say the lifetime of this instrument is undesirably shortened.

To eliminate this problem, a sliding contact has therefore been provided, for the at least one movable jaw part, which taps the current at the hinge forming the pivot axis of the at least one movable jaw part, the current supply line ending accordingly at the hinge. The provision of a sliding contact in the area of the hinge is, however, very complex in terms of construction and is very difficult to achieve, especially in very small instruments.

The document WO-A-01/15614 discloses an electrosurgical medical instrument, in particular a bipolar medical instrument, having two jaw parts, of which one is movable. In the area of their articulated connection, the two jaw parts have a main body made of an electrically insulating material, on which is secured an electrically conductive jaw part insert forming the associated electrode. The current supply to the electrode of the movable jaw part is effected via the axially movable force transmission element provided for opening and closing the jaw parts, while the electrode of the non-movable jaw part via a rectilinear, wire-shaped element which is connected proximally to the tubular shaft likewise serving as current supply and whose distal end is connected to the electrode of the non-movable jaw part.

If the second jaw part were also to be made movable, this would entail the same problem as in the known instrument described above, namely that the wire-shaped element would be permanently subjected to bending and stretching stresses, which in the long run would again lead to fracturing of the wire-shaped element.

SUMMARY OF THE INVENTION

It is therefore an object of the invention to develop a medical instrument of the type mentioned at the outset in such a way that the lifetime of the instrument is increased.

According to an aspect of the invention, a medical instrument for electrosurgery is provided, comprising a tubular shaft having a distal end and a proximal end, at least one jaw part arranged at said distal end of said shaft and movable relative to said tubular shaft about a pivot axis, at least one electrode arranged at said at least one jaw part, and at least one current supply line leading to said at least one electrode and designed as a wire-shaped element, a distal end of which being connected to said at least one electrode, said wire-shaped element being configured as a loop in a region of said pivot axis.

Unlike the known instrument in which the wire-shaped element is routed essentially in a straight line past the hinge forming the pivot axis, in the medical instrument according to the invention the wire-shaped element in the area of the pivot axis is configured as a loop, which ensures a length compensation when the at least one movable jaw part is pivoted about the pivot axis. As the at least one movable jaw part is pivoted to and fro during use of the instrument, the wire-shaped element is thus no longer subjected permanently to bending stresses, because the permanent change of angle of the at least one movable jaw part relative to the shaft is passed on to the loop and is converted by the latter into a length increase or length decrease at the circumference of the loop. The loop accordingly works as a kind of torsion spring.

In a preferred embodiment, the loop extends over at least approximately half a circle.

This measure has the advantage that the total length of the wire-shaped element is only slightly increased compared to a rectilinear, wire-shaped element, and, on the other hand, in medical instruments in which the at least one movable jaw part runs through only a slight maximal pivot angle, is sufficient to provide the above-described effect according to the invention.

It is particularly preferable if the loop extends over at least one full circle.

In this embodiment, the wire-shaped element has at least one complete winding. In this configuration, the proximal end and the distal end of the wire-shaped element form a kind of leg spring, as in a clothes peg, and, for the purposes of the present invention, one winding as a spiral or helical spring is sufficient, although more windings can also be provided.

In a further preferred embodiment, the loop is resilient.

This can advantageously and preferably be realized by the fact that the wire-shaped element, at least in the area of the loop, is made of a resilient material, for example of spring steel. A certain elasticity, however, is already obtained through the bent configuration of the wire-shaped element as loop and can be further increased by the aforementioned choice of material. The elasticity of the loop can advantageously assist the pivoting of the at least one movable jaw part, for example either the opening movement or closing movement of the at least one movable jaw part.

In a further preferred embodiment, the loop is arranged around the pivot axis.

While it may also be possible within the scope of the present invention to arrange the loop distally or proximally from the pivot axis, the aforementioned measure has the advantage that the loop can be arranged at this location without the need for additional space. The further advantage of this measure lies in the fact that the wire-shaped element is most strongly subjected to bending stresses in the area of the pivot axis, and the length compensation effected by the loop is best achieved here.

In a further preferred embodiment, a proximal end of the wire-shaped element is fixed on the tubular shaft and connected conductively to it.

This measure has the advantage that the tubular shaft, as in the known instrument, can be used as current supply line. The proximal end of the wire-shaped element can be fixed in the area of the distal end of the tubular shaft, which has the further advantage that the wire-shaped element does not have to be guided completely through the tubular shaft to the proximal end, thus simplifying the assembly of the instrument according to the invention.

In a further preferred embodiment, the distal end of the tubular shaft is provided with a second movable jaw part which is pivotable about the pivot axis and has a second electrode, and an axially movable force transmission element of an actuating mechanism for moving the two jaw parts serves as a current supply line for the second electrode.

In this embodiment, the advantageous effects of the present invention are of particular note, because a current supply is present for both electrodes of the two movable jaw parts, thus avoiding bending stresses and, consequently, the danger of fracturing.

In this context, it is preferable for the two jaw parts to be insulated from one another in the region of the pivot axis.

As in the instrument known from the document WO-A-01/15614, such insulation can be provided by the jaw parts, or at least one of the two jaw parts, having, in the area of the pivot axis, a main body made of an electrically insulating material. A rivet or pin forming the pivot axis can then be made of metal and thus be made especially stable, since the insulating main body provides electrical separation of the two jaw parts from one another.

Further advantages and features will become evident from the following description and from the attached drawing.

It will be appreciated that the features mentioned above and those still to be explained below can be used not just in the respectively cited combination, but also in other combinations or in isolation, without thereby departing from the scope of the present invention.

BRIEF DESCRIPTION OF THE DRAWINGS

An illustrative embodiment of the invention is shown in the drawing and is described in more detail below with reference to this drawing, in which.

DETAILED DESCRIPTION OF A PREFERRED EMBODIMENT

Figure 1:
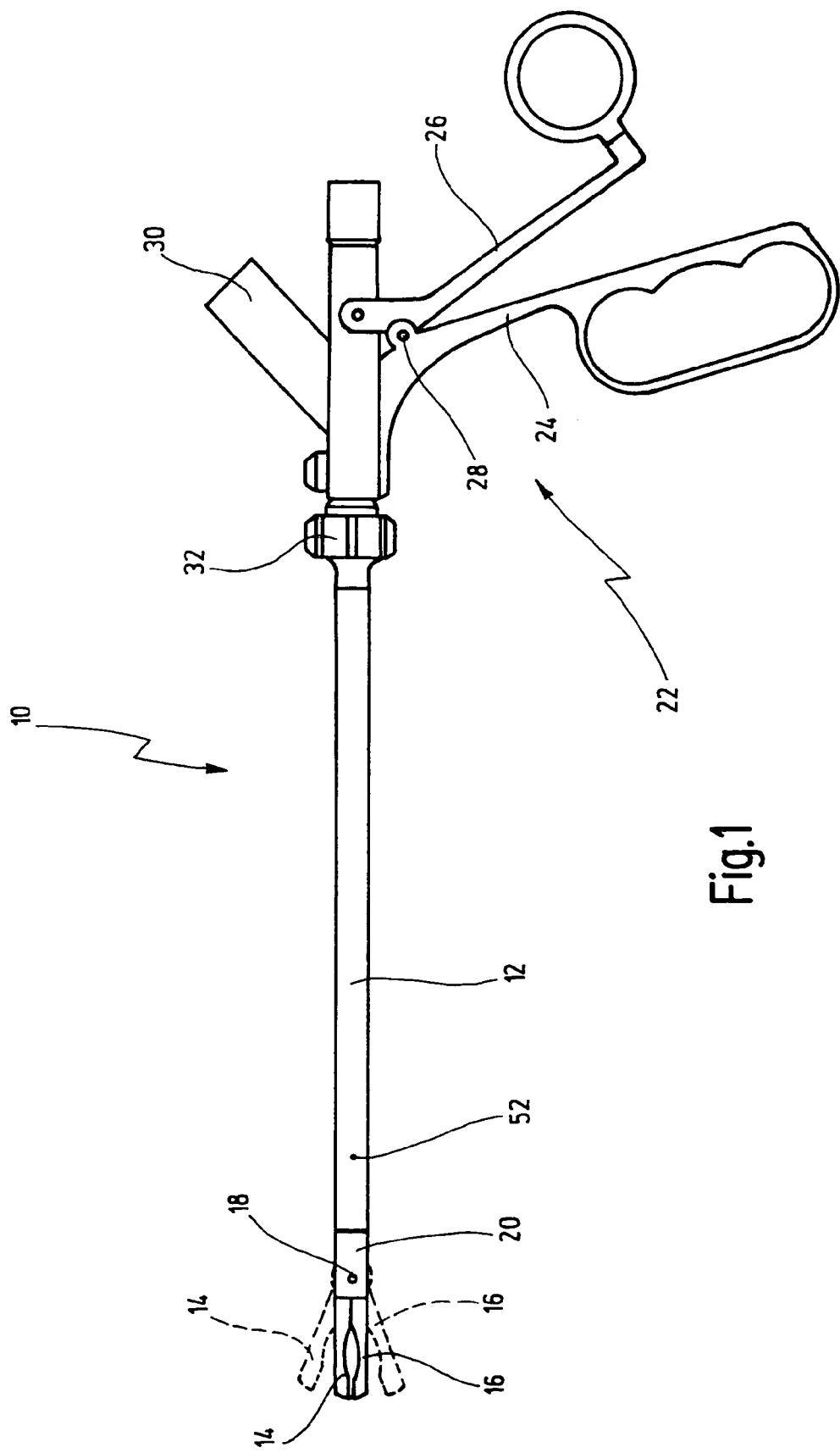
FIG. 1 shows a side view of a medical instrument for electrosurgery.

A medical instrument for electrosurgery is shown by general reference number 10 in FIG. 1. Further particulars of the instrument 10 are shown in more detail in FIG. 2.

In the context of minimally invasive surgery for treatment of tissue in the human or animal body, the instrument 10 is used for dissection by means of high-frequency current.

In the illustrative embodiment shown, the instrument 10 is a gripping instrument, more specifically gripping forceps, with which tissue can be gripped and coagulated. The instrument 10 is also a bipolar instrument, as will be explained in more detail below.

The instrument 10 has an elongate tubular shaft 12. The tubular shaft 12 is a metal tube designed as a current conductor and surrounded by an insulating sheath.

A first jaw part 14 and a second jaw part 16 are arranged at the distal end of the tubular shaft 12.

The first jaw part 14 and the second jaw part 16 are both movable relative to the tubular shaft 12 about a pivot axis 18, that is to say they are pivotable. In FIG. 1, the jaw parts 14 and 16 are shown in their closed position by solid lines and are shown in their open position by broken lines.

In the area of the pivot axis 18, the jaw parts 14 and 16 are secured on an insulator piece 20 which is made of plastic or ceramic and which in turn is connected to the tubular shaft 12.

Arranged at the proximal end of the tubular shaft 12 there is a handle 22 having two grip parts 24 and 26. The grip parts 24 and 26 are connected to one another in an articulated manner so that they can pivot relative to one another about a pivot axis 28, the relative movement of the grip parts 24 and 26 serving to open and close the jaw parts 14 and 16.

The handle 22 is also provided with an attachment 30 for joining the instrument 10 to a high-frequency current generator (not shown).

The tubular shaft 12 can also be turned about its longitudinal axis, for which purpose a rotary knob 32 is arranged on the distal end of the handle 22.

Figure 2:
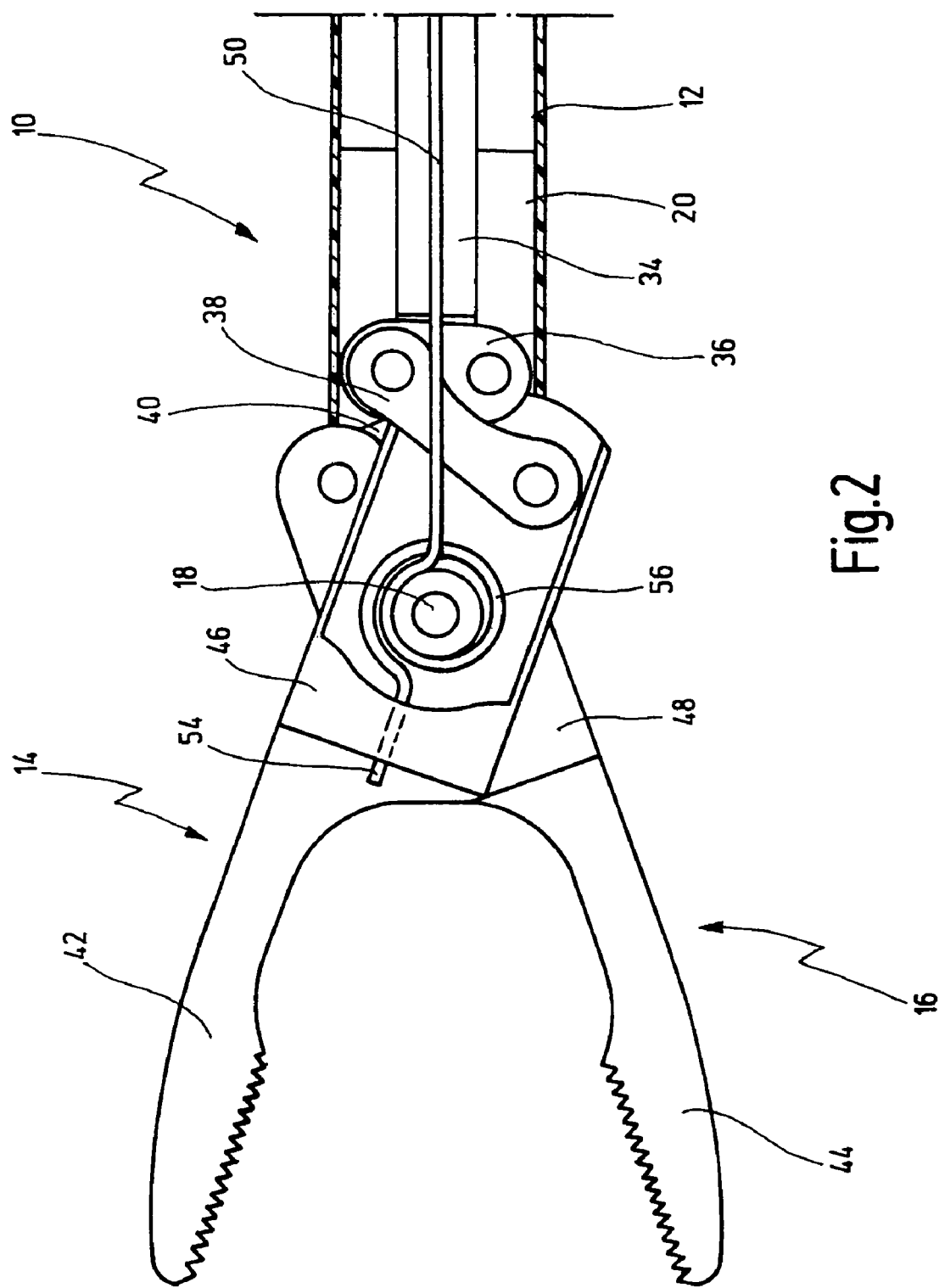
FIG. 2 shows the distal end of the instrument from FIG. 1 on an enlarged scale, and partially in longitudinal section.

Extending through the tubular shaft 12, from the handle 22 to the jaw parts 14 and 16, there is an axially movable force transmission element 34 which, in FIG. 2, is shown in the area of its distal end, and its proximal end is connected to one of the two grip parts 24, 26 with a force fit. The force transmission element 34 is connected to the two jaw parts 14 and 16 via an articulated lever mechanism 36, 38, 40. An axial movement of the force transmission element 34 serves to open and close the jaw parts 14 and 16, that is to say pivot the jaw parts 14 and 16 about the pivot axis 18.

The pivot axis 18 is formed, for example, by a rivet or pin extending transversely with respect to the longitudinal direction of the shaft 12.

Further particulars of the instrument 10 in the area of the jaw parts 14 and 16 are now described in detail with reference to FIG. 2.

The jaw part 14 has an electrode 42, and the jaw part 16 has an electrode 44, the electrodes 42 and 44 forming the distal ends of the jaw parts 14 and 16, respectively.

In the proximal area, the jaw part 14 has a main body 46 made of insulating material, and the jaw part 16 has a main body 48 likewise made of insulating material. In this way, the jaw parts 14 and 16 are electrically insulated from one another in their proximal area.

The current supply line for the electrode 42 of the jaw part 14 is a wire-shaped element 50 whose proximal end is connected to the tubular shaft 12 designed as current conductor, for example in the area of the location labelled with reference number 52 in FIG. 1. The electrode 42 can thus be connected to a first pole of the high-frequency current generator via the tubular shaft 12 and the wire-shaped element 50.

A distal end 54 of the wire-shaped element 50 is connected electrically conductively to the electrode 42.

In the area of the pivot axis 18, the wire-shaped element 50 is configured as a loop 56, which is arranged around the pivot axis 18.

In the present illustrative embodiment, the loop 56 is formed by the wire-shaped element 50 being routed approximately one and a half times round the pivot axis 18 and thus has at least one winding. Upon opening and closing of the jaw part 14, the loop 56 effects a length compensation, the wire-shaped element 50 thus being subjected considerably less to bending or stretching stresses.

Whereas, in the illustrative embodiment shown, the loop 56 thus extends over at least one full circle, the loop 56 can however also extend over at least approximately half a circle, if this satisfies the requirements.

The loop 56 is in particular resilient, for which purpose the wire-shaped element 50 at least in the area of the loop 56 is made of a resilient, electrically conductive material, in particular of spring steel.

By contrast, the electrode 44 of the second jaw part 16 is connected to the other pole of the high-frequency current generator via the force transmission element 34, which is accordingly made electrically conductive, the current transfer from the force transmission element 34 via the articulated lever mechanism 36, 40 taking place in the manner described in the document WO-A-01/15614, the content of which is in this regard expressly incorporated herein by reference.

What is claimed is:

1. A medical instrument for electrosurgery, comprising:
   a tubular shaft having a distal end and a proximal end,
   at least one jaw part arranged at said distal end of said shaft and movable relative to said tubular shaft about a pivot axis,
   at least one electrode arranged at said at least one jaw part,
   at least one current supply line leading to said at least one electrode and designed as a wire-shaped element, a distal end of which being connected to said at least one electrode, said wire-shaped element being configured as a loop in the region of said pivot axis;
   said wire-shaped element, at least in the region of said loop, is made of a resilient, electrically conductive material; and said wire-shaped element is made of spring steel, at least in the region of said loop.

2. The instrument of claim 1, wherein said loop extends over at least approximately half a circle.

3. The instrument of claim 1, wherein said loop extends over at least one full circle.

4. The instrument of claim 1, wherein said loop is arranged around said pivot axis.

5. The instrument of claim 1, wherein said distal end of said tubular shaft is provided with a second moveable jaw part which is pivotable about said pivot axis and has a second electrode, and wherein an axially moveable force transmission element of an actuating mechanism for moving said two jaw parts serves as current supply line for said second electrode.

6. The instrument of claim 5, wherein said two jaw parts are insulated from one another in the region of said pivot axis.

7. A medical instrument for electrosurgery, comprising:
   a tubular shaft having a distal end and a proximal end,
   at least one jaw part arranged at said distal end of said shaft and movable relative to said tubular shaft about a pivot axis,
   at least one electrode arranged at said at least one jaw part, and
   at least one current supply line leading to said at least one electrode and designed as a wire-shaped element, a distal end of which being connected to said at least one electrode, said wire-shaped element being configured as a loop in the region of said pivot axis; and
   wherein a proximal end of said wire-shaped element is fixed on said tubular shaft and connected conductively to said tubular shaft.

8. The instrument of claim 7, wherein said loop is resilient.

9. The instrument of claim 7, wherein said distal end of said tubular shaft is provided with a second moveable jaw part which is pivotable about said pivot axis and has a second electrode, and wherein an axially moveable force transmission element of an actuating mechanism for moving said two jaw parts serves as current supply line for said second electrode.

10. The instrument of claim 9, wherein said two jaw parts are insulated from one another in the region of said pivot axis.

11. The instrument of claim 7, wherein said loop is arranged around said pivot axis.

* * * * *